United States Patent [19]

O'Leary et al.

[11] Patent Number: 5,667,985

[45] Date of Patent: Sep. 16, 1997

[54] TISSUE BIOPSY CELL SUSPENDER FOR CELL ANALYSIS

[75] Inventors: Robert K. O'Leary, Lexington, Mass.; Timothy Stevens, Warwick, N.Y.; Richard L. Griffith, Allendale, N.J.

[73] Assignee: Becton Dickinson and Company, Franklin Lakes, N.J.

[21] Appl. No.: 718,850

[22] Filed: Sep. 24, 1996

[51] Int. Cl.$^6$ .............................. C12Q 1/02; C12M 3/00
[52] U.S. Cl. .................... 435/29; 435/40.51; 435/40.52; 435/287.6; 435/810
[58] Field of Search ................................. 435/1.1, 2, 283.1, 435/284.1, 287.6, 4, 29, 40.51, 40.52, 810; 422/61

[56] References Cited

U.S. PATENT DOCUMENTS

| | | | |
|---|---|---|---|
| 4,461,837 | 7/1984 | Karle, et al. | 435/296 |
| 4,732,850 | 3/1988 | Brown et al. | 435/31 |
| 5,073,488 | 12/1991 | Matner et al. | 435/31 |

FOREIGN PATENT DOCUMENTS 9609529  3/1996  WIPO.

OTHER PUBLICATIONS

"Cell Isolation Theory," Worthing Manual Tissue Dissociation Guide, Pp. 2–14.
"Culture Of Animal Cells," by R. Ian Freshney, Wiley–Liss, pp. 116–125.
"Cell Culture," by William B. Jakoby and Ira H. Pastan, Methods in Enzymology, pp. 119–130.

"Worthing Enzyme Manual, enzymes, enzyme reagents, related biochemicals," Worthington Biochemical Corporation, (1972), pp. 125–127.

"Neuropathology Of AIDS In Surgical Biopsy Specimens," by Douglas C. Miller, MD, PhD, Souhel Najjar, MD and Gleb N. Budzilovich, MD, Neurosurgery Clinics of North America, vol. 5, No. 1, Jan. 1994, pp. 57–70.

*Primary Examiner*—David A. Redding
*Attorney, Agent, or Firm*—Arthur D. Dawson

[57] ABSTRACT

A tissue biopsy cell suspender device includes a receptacle having a sealable opening. The receptacle contains a sufficient quantity of an aqueous medium to support an enzymatic dissociation of cells from a tissue biopsy sample. The device has a removable closure with a first sealing position and a second sealing position for sealing the opening in the receptacle. The device further includes a frangible container having a sufficient quantity of an enzyme therein to dissociate cells from the tissue biopsy sample. The frangible container is covered with a membrane that is permeable to water and to the enzyme. The frangible container is disposed within the receptacle so that the container is intact when the closure is in the first sealing position and the container is breached when the closure is in the second sealing position. When the frangible container is breached, the enzyme is released to permeate into the medium and for dissociation of the cells from the tissue sample.

17 Claims, 4 Drawing Sheets

FIG-2
FIG-3
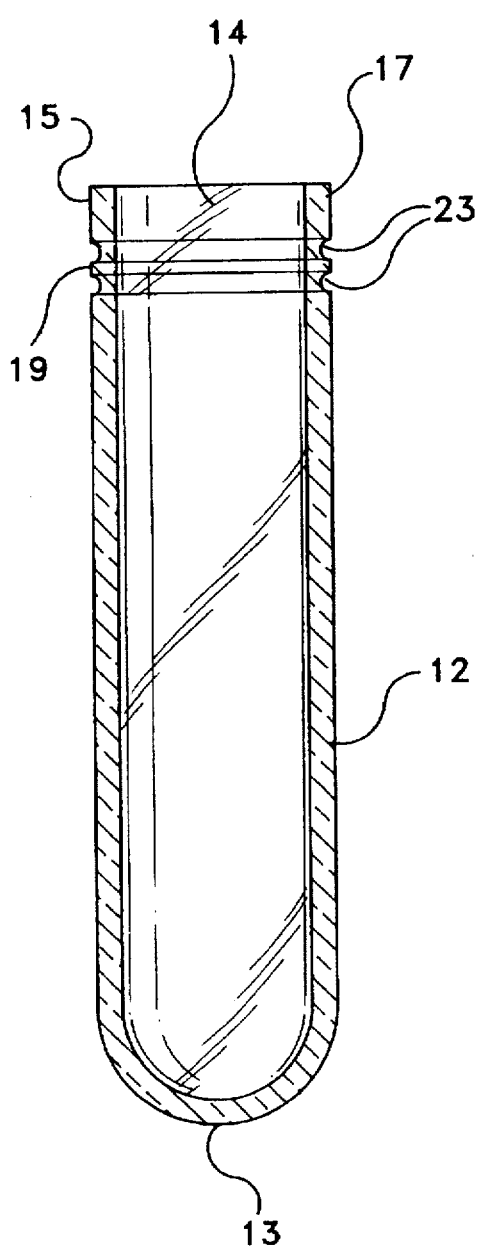
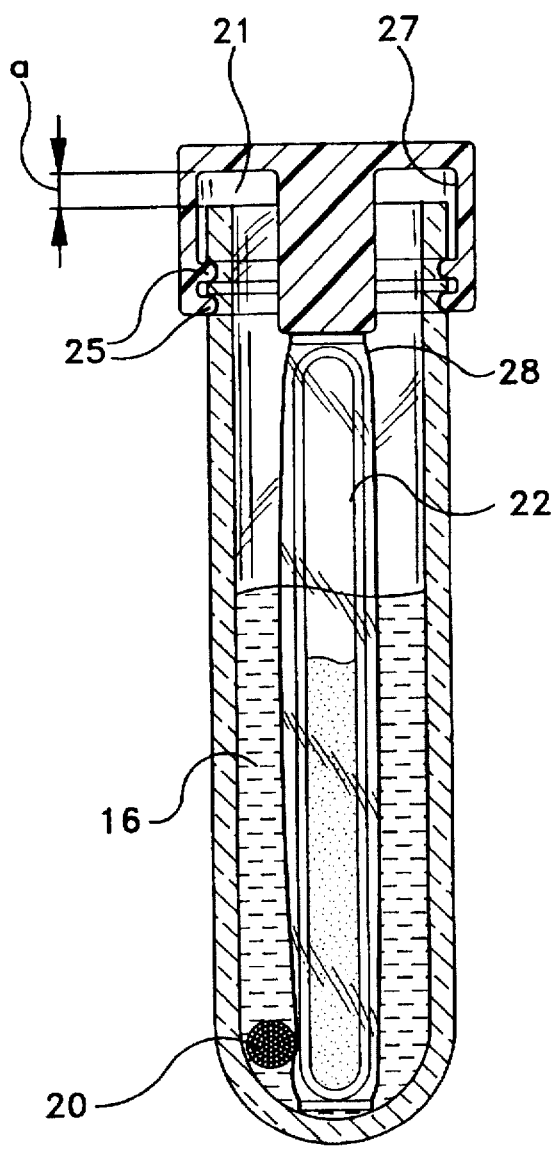

TISSUE BIOPSY CELL SUSPENDER FOR CELL ANALYSIS

FIELD OF THE INVENTION

The invention is generally related to preparation of biopsy samples for analysis, and more particularly a device and a method to facilitate enzymatic release of intact cells from tissue samples.

BACKGROUND

Microscopic examination of biopsy material is an essential component of many diagnostic procedures. There are many different biopsy techniques. Many biopsy procedures are performed in an operating room setting with the patient under anesthesia. A biopsy is often performed to confirm a diagnosis and, as soon as the finding from the biopsy is received, and the original diagnosis is confirmed, the practitioner performs a surgical procedure. Generally, the biopsy sample is transmitted to a lab where the tissue sample is sectioned, stained and microscopically examined. Since in many cases, the patient is already under anesthesia, any time spent transporting the biopsy specimen to a remote laboratory, subjects the patient to additional risk associated with prolonged anesthesia.

Biopsy techniques may be divided into closed and open methods. Closed techniques include aspiration (for cysts), aspiration for cytology (for suspected carcinoma) and core biopsy for histology. Open techniques include incisional biopsy, excisional biopsy and needle localization biopsy. Lung biopsy is often performed with a bronchoscope and a grasper or a brush is used to obtain the sample of the target tissue. A technique now being used more frequently is the Fine Needle Aspiration Biopsy. Many of these biopsy techniques only yield a small sample of tissue.

Once the tissue sample is obtained, it must be prepared for evaluation. One commonly used technique requires the sample to be frozen, sectioned on a microtome, stained and microscopically evaluated. The freezing and sectioning procedures are time consuming. Tissue samples also are fixed in formalin, embedded in paraffin and sectioned on a microtome. Fixation in formalin and embedding in paraffin requires a fume hood as formalin is considered toxic and is strongly irritating to mucous membranes. In another commonly practiced technique, the tissue sample may be partially digested with enzymes to free cells from the connective tissue for microscopic evaluation.

Sample preparation and evaluation practices vary from institution to institution. In many cases, practitioners who would otherwise prefer to have rapid evaluation of a biopsy specimen conducted as part of the biopsy procedure, are required to transmit the sample to a remote laboratory for evaluation because an enzymatic digestion of the sample to provide free cells is required. The transmission to the laboratory is required because the enzymatic work-up requires laboratory facilities to prepare the enzyme solution in a suitable medium. If a system were available that included appropriate amounts of enzyme and a suitable medium for the enzymatic dissociation of the cells from the connective tissue, the art of rapid evaluation of a biopsy sample would be advanced. Such a device and a method for its use are described herein below.

SUMMARY

A tissue biopsy cell suspender device of the present invention includes a receptacle having a sealable opening. The receptacle contains a sufficient quantity of an aqueous medium to support an enzymatic dissociation of cells from a tissue biopsy sample. The device has a removable closure with a first sealing position and a second sealing position for sealing the opening in the receptacle. The device further includes a frangible container having a sufficient quantity of an enzyme therein to dissociate cells from the tissue biopsy sample. The frangible container is covered with a membrane that is permeable to water and to the enzyme. The frangible container is disposed within the receptacle so that the container is intact when the closure is in the first sealing position and the container is breached when the closure is in the second sealing position. When the frangible container is breached, the enzyme is released to permeate into the medium and for dissociation of the cells from the tissue sample.

The self-contained device of the invention is particularly well-suited for fine needle biopsy or other small mass biopsy sample techniques directly in operating room suites. In much current practice, a practitioner obtains a fine-needle biopsy tissue sample and arranges for its transport to a remote laboratory for evaluation. The tissue biopsy cell suspender of the invention provides the practitioner with a self-contained complete package of reagents and the reaction vessel to obtain intact cells for microscopic evaluation at the location of the biopsy. The device of the invention is provided sterile and ready-to-use with sufficient quantities of both medium and enzyme to dissociate the cells from the tissue sample. The medium and the enzyme are kept separate from each other and are sterile until ready to use, providing shelf stability not currently available to the biopsy evaluation art. The practitioner removes the closure from the receptacle, introduces the sample into the receptacle and replaces the closure moving it to breach the frangible container and release the enzyme into the medium. After an incubation period, the dissociated cells are collected for a microscopic examination to allow the practitioner to confirm the diagnosis and continue. The membrane covering the frangible container of the invention serves to limit the concentration of the enzyme released into the medium and substantially reduces the criticality of the timing of the incubation period between the initiation of the enzymatic process by breaching the frangible container and the collection of sufficient cells for evaluation, particularly for small mass biopsy samples.

BRIEF DESCRIPTION OF THE DRAWINGS

FIG. 2 is a cross-sectional view of the receptacle portion of the invention of FIG. 1;

FIG. 3 is a cross-sectional view of the invention of FIG. 1 assembled and charged with a specimen;

DETAILED DESCRIPTION

Figure 1:
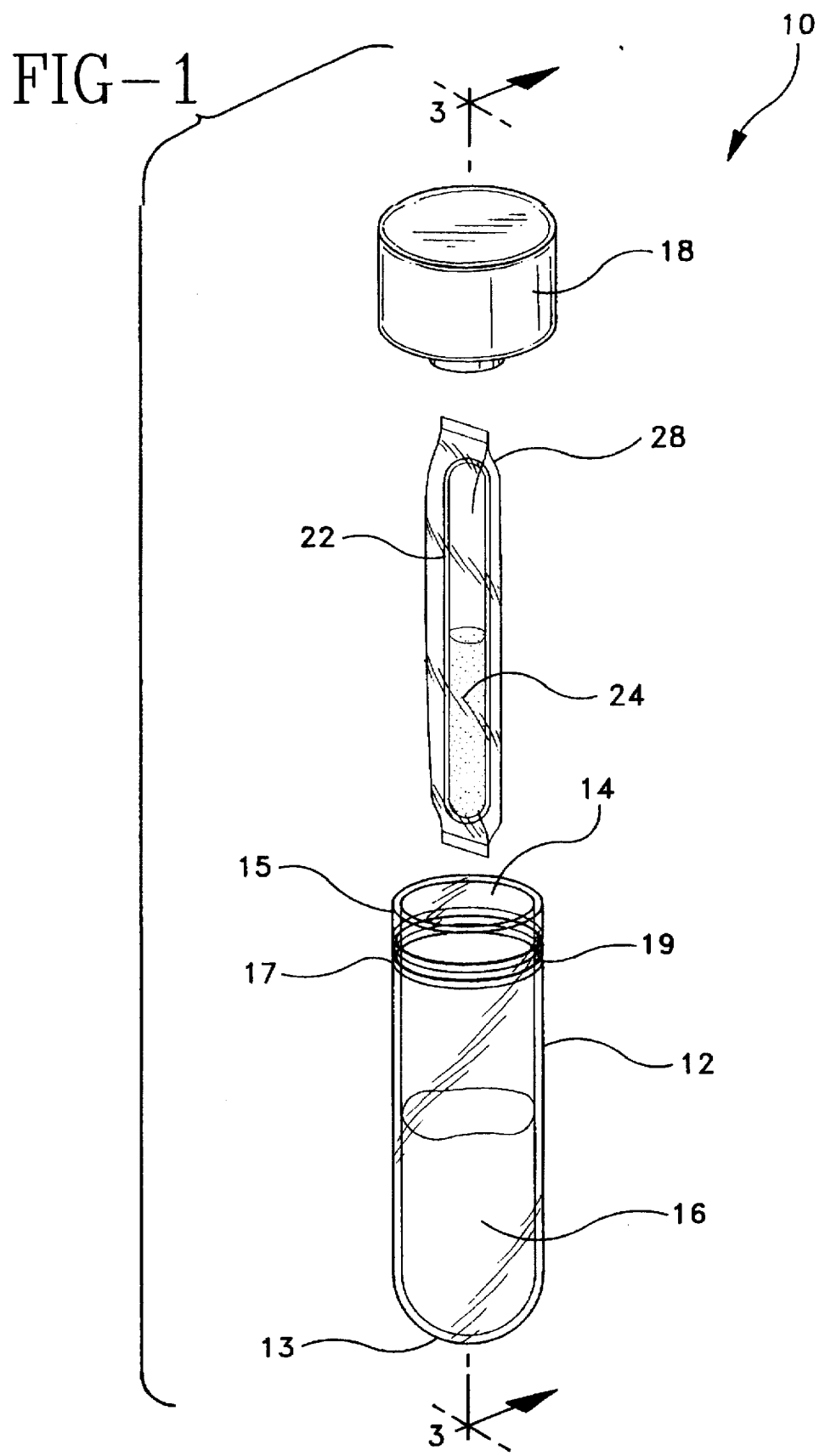
FIG. 1 is an exploded perspective view of the tissue biopsy cell suspender device of the invention.

While this invention is satisfied by embodiments in many different forms, there is shown in the drawings and herein described in detail, a preferred embodiment of the invention with the understanding that the present disclosure is to be considered exemplary of the principles of the invention and is not considered to limit the invention to the embodiment illustrated. The scope of the invention is measured by the appended claims and their equivalents.

Figure 4:
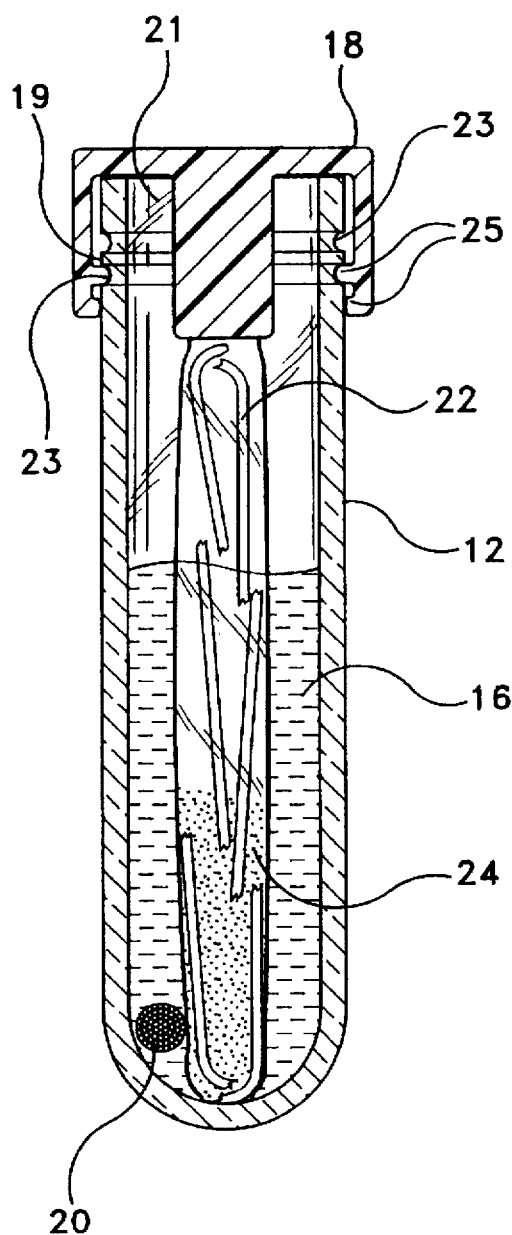
FIG. 4 is a cross-sectional view of the invention of FIG. 1 illustrating the closure in the second position.
Figure 5:
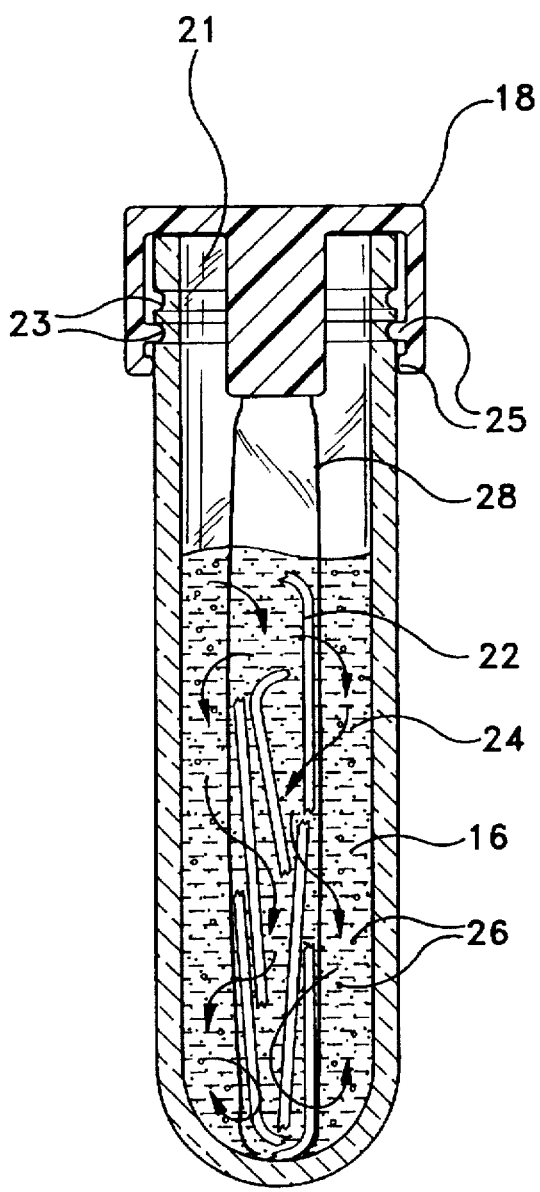
FIG. 5 is a cross-sectional view of the invention of FIG. 1 after incubation.

Referring to FIGS. 1–6, a preferred tissue biopsy cell suspender device 10 of the present invention includes a receptacle 12 having a sealable opening 14. Receptacle 12 contains a sufficient quantity of an aqueous medium 16 to support an enzymatic dissociation of cells from a tissue biopsy sample 20. Device 10 has a removable closure 18 with a first sealing position, best seen in FIG. 3, and a second sealing position, best seen in FIGS. 4 and 5, for sealing opening 14 in receptacle 12. Device 10 further includes a frangible container 22 having a sufficient quantity of an enzyme 24 therein to dissociate cells 26 from tissue biopsy sample 20. Frangible container 22 is covered with a membrane 28 that is permeable to water and to the enzyme. Frangible container 22 is disposed within receptacle 12 so that container 22 is intact when closure 18 is in the first sealing position and container 22 is breached when closure 18 is in the second sealing position as shown in FIGS. 4 and 5. When frangible container 22 is breached, enzyme 24 is released to permeate through membrane 28 into medium 16 and for dissociation of cells 26 from the tissue sample. Membrane 28 serves to limit the concentration of enzyme available to the tissue sample to a concentration sufficient to free cells from the connective tissue but substantially below an enzyme concentration that would also degrade the cells. If membrane 28 were not present, the entire amount of the enzyme would be released upon the breaching of frangible container 22. In cases where the biopsy sample has only a small mass, the high enzyme concentration would rapidly result in degradation of the cells as well as the connective tissue. If membrane 28 were not present the time between the initiation of the enzymatic process started by breaching frangible container 22 and for collecting sufficient freed cells for the evaluation would be need to be carefully monitored in order to prevent the degradation of the cells. Since membrane 28 limits the enzyme concentration, the timing between the initiation of the enzyme process and the collection of sufficient cells for the evaluation is much less critical.

Preferably, receptacle 12 has a tubular shape with a closed end 13 and an open end 15 with a neck 17 that has at least one detent 19 to engage closure 18 when closure is positioned to seal opening 14 thereby defining the first sealing position. Closure 18 is preferably formed from a resilient material and includes a socket 21 for receiving neck 17 of receptacle 12. Detent 19 preferably includes at least one groove 23 on neck 17 positioned to releasably engage at least one inward shoulder 25 on an inside surface 27 of socket 21. Socket 21 has sufficient clearance, illustrated by distance "a" in FIG. 3, to allow closure 18 be moved further onto neck 17 beyond detent 19 to the second sealing position, seen in FIGS. 4 and 5, to breach frangible container 22. Preferably, detent 19 includes a second groove 29 on inside surface 27 to define the second sealing position. Placement of shoulder 25 in second groove 29 substantially ensures that frangible container 22 is breached and the enzyme is released into the medium through permeable membrane 28.

Figure 6:
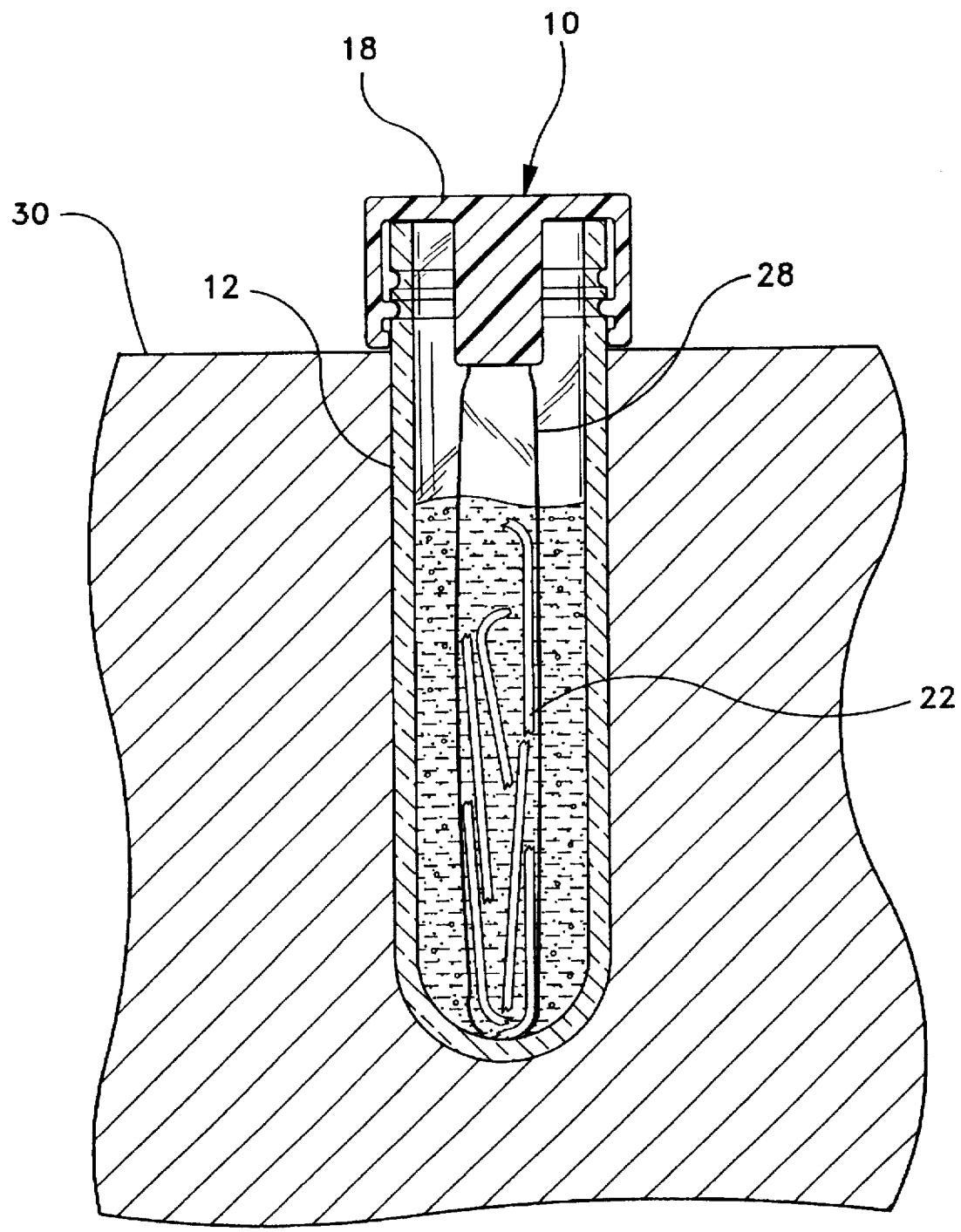
FIG. 6 is a cross-sectional view of the invention of FIG. 1 in a thermostat.

Since device 10 is supplied charged with medium, it is supplied sterile with closure 18 in the first position to preclude microbial growth in the medium prior to usage. Device 10 may sterilized after assembly by exposure to conditions that are capable of rendering any microorganisms present non-viable. Alternatively, the several components of device 10 may be sterilized before assembly with the assembly and medium charging being conducted under substantially sterile conditions. By keeping the enzyme separate from the medium and sterile until the closure is removed, the preferred device provides a system that is stable to shelf storage stable and that is ready for the practitioner's use. When a practitioner is ready to introduce a tissue sample, the practitioner simply removes closure 18, places the tissue sample into receptacle 12, replaces the closure, and moves the closure to the second sealing position to breach container 22 to release the enzyme. As shown in FIG. 6, the sealed receptacle may then be placed in an incubating device 30 to maintain the enzyme, medium and tissue suspension at a suitable temperature, preferably about 37° C. for sufficient time to allow the enzyme to dissociate the cells from the tissue. The receptacle is then preferably cooled to substantially quench the enzymatic reaction and sufficient cells withdrawn for the desired examination.

Alternatively, device 10 may be used as a transport device for transporting the tissue sample to a laboratory. When device 10 is used in this fashion, the practitioner removes closure 18, introduces the tissue sample and replaces the closure to the first position to seal the receptacle. If device 10 with the tissue sample is maintained at about 0° C. to about 4° C., the tissue sample is substantially stable for up to about twelve hours. When used as a transport device, closure 18 may be moved to the second position on the receptacle to breach the frangible container at the laboratory and begin the sample preparation process without additional handling.

Minimum Essential Medium (M.E.M.), Balanced Salts Solution (B.S.S.) and the like are suitable for supporting the enzymatic dissociation of cells from the tissue sample when the enzyme is chymopapian, papain, trypsin, chymotrypsin and the like. M.E.M. contains salts, glucose and amino acids and is preferred for the present invention. Other enzymes and other media may be preferred for particular applications. The particular medium selected should be evaluated for shelf stability after the particular sterilization technique selected. The amount of the medium placed in the receptacle depends upon the size of the biopsy sample intended to be processed. Generally, for biopsy samples with a mass between about 0.5 grams to about 1.5 grams, a volume of medium between about 0.5 ml to about 5.0 ml is satisfactory. For particular applications, and samples having larger or smaller masses, larger or smaller volumes of medium may be preferred and are considered within the scope of the invention.

Suitable collagenase preparations are available from Worthington Biochemical Corporation, Freehold, N.J., and are characterized as Types I–IV. Type I has a "normal balance" of enzyme activities, and is recommended for at cells and adrenal tissue; Type II is high in clostripain activity, and is recommended for liver, bone, thyroid, heart and salivary tissue; Type III is low in proteolytic activity, and is recommended for mammary tissue; and Type IV has low tryptic activity and is recommended for pancreatic islets. Other individual enzymes such as pronase, collagenase, trypsin, hyaluronidase, amylase, elastase, pancreatin, papain, chymopapain, chymotrypsin, ribonuclease and deoxyribonuclease are suitable as well as mixtures of one or more of these enzymes. Enzymes such as those listed above are widely commercially available and the techniques of drying, freeze drying and the like for preparation of isolated stable enzymes for placement in sealed container 22 are well known. One skilled in the art of enzymes recognizes that virtually all of these enzymes normally contain several activities. Crude trypsin may contain in addition to trypsin, chymotrypsin, elastase, ribonuclease, deoxyribonuclease and amylase. For particular applications, any or all of these enzymes either singly or in mixtures are suitable for use in the invention and are considered within the scope of the invention.

The most widely used unit of enzyme activity is defined as that amount of enzyme that causes transformation of 1.0 micromole of substrate per minute at 25° C. Under optimal conditions of measurement. The specific activity is the number of enzyme units per milligram of protein. The international unit for enzyme activity recommended by the Enzyme Commission is the "katal" (abbreviated "kat") and is defined as the amount of enzyme activity that transforms one mole of substrate per second. The international unit is in accord with the dimensions of rate constants in chemical kinetics, which are based on the second rather than the minute. Activities can also be given in microkatals, nanokatals or picokatals.

Several examples illustrate enzyme content of the container suitable for tissue samples between with mass between about 0.25 grams to about 1.0 grams. In these examples, the medium used is about one milliliter of M.E.M.

EXAMPLES

1.) Sufficient collagenase to form a concentration of about 43 nanokat to about 51 nanokat per milliliter;
2.) Sufficient chymopapain to form a concentration of about 0.22 nanokat to about 0.44 nanokat; and
3.) A sufficient quantity of a mixture of purified collagenase and chymopapain to produce a concentration of about 50 nanokat collagenase and 0.25 nanokat of chymopapain in about 1 ml of M.E.M. This amount of medium with about these enzyme concentrations is sufficient to release about 8,000 to about 10,000 isolatable cells from an about one gram biopsy tissue sample in about five minutes. Eight to about ten thousand cells is a sufficient quantity for histopathological diagnosis.

Receptacle 12 may be formed from glass or polymeric materials such as polycarbonate, polyvinyl chloride, polystyrene and the like. Preferably, receptacle 12 is formed from glass. Frangible container 22 may be formed from a material that will maintain a proper storage environment for the enzyme selected and keep the enzyme isolated from the aqueous medium. Preferably, frangible container 22 is formed from glass that can be easily breached when closure 18 is moved to the second position after the biopsy sample has been introduced into the receptacle.

Preferred membrane 28 has a multiplicity of pores sized between about 0.1 microns and 10 microns with a pore density of between about $0.1 \times 10^6$ to about $10.0 \times 10^6$ per square centimeter and allows the passage of water and enzyme It is believed that the rate of transmission of enzyme through the membrane is described by Fick's law of diffusion, i.e., the flow is proportional to the gradient of concentration. Since the diffusion of the enzyme through membrane limits the release of the enzyme into the medium, the timing after breaching frangible container 22 to the collection free cells for evaluation is substantially less critical than it would without the membrane, particularly with small mass samples. Suitable membranes may be formed from materials such as deacetylated cellulose heat sealable film, polyethylene terephthalate film, polycarbonate film, polypropylene film. Frangible container 22 is sealed in membrane 28, suitable sealing techniques included crimps adhesive bonding at the ends of the membrane cover, heat sealing and ultrasonic bonding. Preferably, membrane 28 is formed in a tubular shape, as shown in FIGS. 1–3, frangible container 22 placed inside and heat sealed at the ends. The material used to form membrane 28 should be sufficiently resistant to penetration by the material used to form frangible container 22 after the container is breached. If membrane 28 is not resistant to puncture, the rate of release of the enzyme from the container will be more rapid than intended and may result in the cells being attacked by the enzyme as well as the intended release of intact cells from the tissue. Membranes formed from polyethyleneterephtalate with a thickness between about 15 microns and 30 microns are preferred for their resistance to penetration.

Closure 18 may be formed from natural rubber, polyethylene, polypropylene and the like. The material selected to form closure 18 needs to have sufficient resiliency to form a releasable seal when device 10 is assembled, be easily removed by the practitioner to introduce the biopsy sample and be sufficiently rigid to breach frangible container 22 to initiate the enzymatic release when closure 18 is moved to the second position. Additionally, since the medium is supplied in receptacle 12, closure 18 must form a sufficiently tight seal to ensure that the aqueous medium concentration remains substantially constant and sterility is preserved during shelf storage.

The self-contained ready-to-use tissue biopsy cell suspender device of the invention is particularly well suited for biopsy samples of small mass in operating room situations. The device of the invention provides practitioners with an easy-to-use system to free cells from tissue samples for rapid microscopic evaluation.

What is claimed is:
1. A tissue biopsy cell suspender device comprising:
  a receptacle having a sealable opening, said receptacle containing a sufficient quantity of an aqueous medium suitable to support an enzymatic dissociation of cells from a tissue biopsy sample;
  a removable closure for sealing said opening, said closure having a first sealing position and a second sealing position; and
  a frangible container having a sufficient quantity of an enzyme therein to dissociate cells from the tissue biopsy sample, said frangible container being covered with a permeable membrane, said membrane being permeable to water and to said enzyme, said frangible container being disposed within said receptacle so that said container is intact when said closure is in said first sealing position, said container being breached when said closure is in said second sealing position, thereby to release said enzyme to permeate through said membrane into said medium.

2. The device of claim 1 wherein said receptacle is a tube having a closed end and an open end having a neck, said neck having at least one detent to engage said closure when said closure is positioned to seal said opening thereby defining said first sealing position.

3. The device of claim 2 wherein said closure is a resilient stopper comprising a socket having an inside surface with an inward shoulder thereon for receiving said neck of said tube, and wherein said detent comprises a groove on said tube positioned to releasably engage said shoulder.

4. The device of claim 2 wherein said socket further comprises a sufficient clearance to allow said closure to be moved onto said neck to beyond said detent to said second sealing position thereby breaching said frangible container.

5. The device of claim 1 wherein said medium is selected from the group consisting of aqueous minimum essential medium (M.E.M.) and balanced salts solution, (B.S.S.).

6. The device of claim 1 wherein said enzyme is selected from the group consisting of collagenases of the type I, type II, type III and type IV, ribonuclease, deoxribonuclease, amylase, hyaluronidase, elastase, papain, chymopapain, chymotrypsin, trpysin and mixtures thereof.

7. The device of claim 6 wherein said sufficient quantity of said enzyme comprises sufficient enzyme to provide a concentration of said enzyme in said medium between about 0.2 nanokatals to about 0.6 nanokatals.

8. The device of claim 1 wherein said frangible container is formed from glass, said enzyme being lyophilized and sealed in said container.

9. The device of claim 1 wherein said membrane is selected from the group consisting of decacetylated cellulose heat sealable film, polyethylene terephthalate film, polycarbonate film, polypropylene film.

10. The device of claim 9 wherein said membrane has a multiplicity of pores sized between about 0.1 microns and 10 microns with a pore density of between about $0.1 \times 10^6$ to about $10.0 \times 10^6$ per square centimeter.

11. The device of claim 10 wherein said membrane has a thickness between about 15 microns and 30 μm.

12. The device of claim 11 wherein said membrane is formed from polyethylene terephthalate film with a thickness between about 20 microns and 30 microns and has between about $0.1 \times 10^6$ and $10 \times 10^6$ pores per square centimeter.

13. A tissue biopsy cell suspender device comprising:
a tubular receptacle with a capacity between about one and five ml having a sealable opening, said receptacle containing between about 0.5 ml to about 1.5 ml of an aqueous minimum essential medium (M.E.M) to support an enzymatic dissociation of cells from a tissue biopsy sample;
a removable closure for sealing said opening, said closure having a first sealing position and a second sealing position; and
a frangible glass container having a sufficient quantity of an enzyme therein to dissociate cells from the tissue biopsy sample, said frangible container being covered with a permeable polyethylene terephthalate membrane, said membrane being permeable to water and to said enzyme, said frangible container being disposed within said receptacle so that said container is intact when said closure is in said first sealing position, said container being breached when said closure is in said second sealing position, thereby to release said enzyme to permeate through said membrane into said medium.

14. The device of claim 13 wherein said enzyme is collagenase in sufficient quantity to form a concentration of between about 43 nanokatals to about 51 nanokatals per milliliter in said medium.

15. The device of claim 13 wherein said enzyme is chymopapain in sufficient quantity to form a concentration of between about 0.22 nanokatals to about 0.44 nanokatals per milliter in said medium.

16. The device of claim 13 wherein said enzyme is a mixture of sufficient collagenase to form a concentration of between about 43 nanokatals to about 51 nanokatals per milliliter plus sufficient chymotrypsin to form a concentration of about 0.25 nanotakals per milliliter.

17. A method for releasing intact cells for analysis from a tissue biopsy sample comprising:
providing a sample of tissue from a biopsy;
removing a resealable closure from an opening of a tissue cell suspender device having a receptacle, said receptacle containing a sufficient quantity of an aqueous medium to support an enzymatic dissociation of cells from a tissue biopsy sample wherein said closure has a first sealing position and a second sealing position, said receptacle having a frangible container having a sufficient quantity of an enzyme therein to dissociate cells from the tissue biopsy sample, said frangible container being covered with a permeable membrane, said membrane being permeable to water and to said enzyme, said frangible container being disposed within said receptacle so that said container is intact when said closure is in said first sealing position, said container being breached when said closure is in said second sealing position, thereby to release said enzyme to permeate into said medium;
introducing the tissue sample into said tissue cell suspender device;
replacing said closure thereby sealing said receptacle;
moving said closure to said second sealing position, thereby breaching said frangible container and releasing said enzyme into said medium; and
incubating said tissue sample container for a sufficient time to allow said enzyme to permeate into said medium and dissociate the cells from said tissue.

* * * * *